US009128066B2

(12) United States Patent
Zimmer et al.

(10) Patent No.: US 9,128,066 B2
(45) Date of Patent: Sep. 8, 2015

(54) SYSTEM AND METHOD FOR ANALYZING A BODY FLUID

(75) Inventors: Volker Zimmer, Morbach (DE); Wolfgang Petrich, Bad Schönborn (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 934 days.

(21) Appl. No.: 13/183,976

(22) Filed: Jul. 15, 2011

(65) Prior Publication Data
US 2012/0006105 A1   Jan. 12, 2012

Related U.S. Application Data

(63) Continuation of application No. PCT/EP2010/050395, filed on Jan. 14, 2010.

(30) Foreign Application Priority Data

Jan. 16, 2009   (EP) .................................. 09150807

(51) Int. Cl.
*G01N 1/10*   (2006.01)
*C12M 1/34*   (2006.01)
*C12Q 1/14*   (2006.01)
(Continued)

(52) U.S. Cl.
CPC ........ *G01N 35/00009* (2013.01); *A61B 5/1411* (2013.01); *A61B 5/14532* (2013.01); *A61B 5/15146* (2013.01); *A61B 5/1455* (2013.01); *A61B 2562/0295* (2013.01); *G01N 33/487* (2013.01)

(58) Field of Classification Search
CPC .. A61B 5/1411; A61B 5/145; A61B 5/14546; A61B 5/1455; G01N 33/487
See application file for complete search history.

(56) References Cited

U.S. PATENT DOCUMENTS

| 5,801,057 A | 9/1998 | Smart et al. |
| 7,708,948 B2 | 5/2010 | Petrich |

(Continued)

FOREIGN PATENT DOCUMENTS

| EP | 1362551 A1 | 11/2003 |
| WO | 2005006985 A2 | 1/2005 |
| WO | 2005084530 A2 | 9/2005 |
| WO | 2005084545 A1 | 9/2005 |
| WO | 2005084546 A2 | 9/2005 |

OTHER PUBLICATIONS

Frederick, K. R. et al. "Glucose oxidase from *Aspergillus niger*. Cloning, gene sequence, secretion from *Saccharomyces cerevisiae* and kinetic analysis of a yeast-derived enzyme." J. Biol. Chem. (1990) 265 3797-3802.*

*Primary Examiner* — Christopher A Hixson
(74) *Attorney, Agent, or Firm* — Harness, Dickey

(57) ABSTRACT

The invention concerns a system for analyzing a body fluid comprising a collecting element which receives the body fluid in a reservoir, a test element designed to detect an analyte in the body fluid, a transfer device for making a fluidic connection between the collecting element and the test element, and a detection unit which detects an analyte-specific measurement signal on the test element during a measurement interval. According to the invention it is proposed that the transfer device always brings the test element into contact with the body fluid located in the reservoir during the measurement interval and that the transfer device is configured to physically separate the test element and the collecting element from one another after the measurement interval.

14 Claims, 2 Drawing Sheets

(51) Int. Cl.
  *C12Q 1/70* (2006.01)
  *C12Q 1/04* (2006.01)
  *G01N 35/00* (2006.01)
  *A61B 5/15* (2006.01)
  *A61B 5/145* (2006.01)
  *A61B 5/151* (2006.01)
  *A61B 5/1455* (2006.01)
  *G01N 33/487* (2006.01)

(56) References Cited

U.S. PATENT DOCUMENTS

| | | |
|---|---|---|
| 2005/0137471 A1 | 6/2005 | Haar et al. |
| 2006/0173380 A1 | 8/2006 | Hoenes et al. |
| 2007/0038149 A1* | 2/2007 | Calasso et al. ............... 600/583 |
| 2008/0200887 A1* | 8/2008 | Haar et al. ............... 604/322 |

* cited by examiner

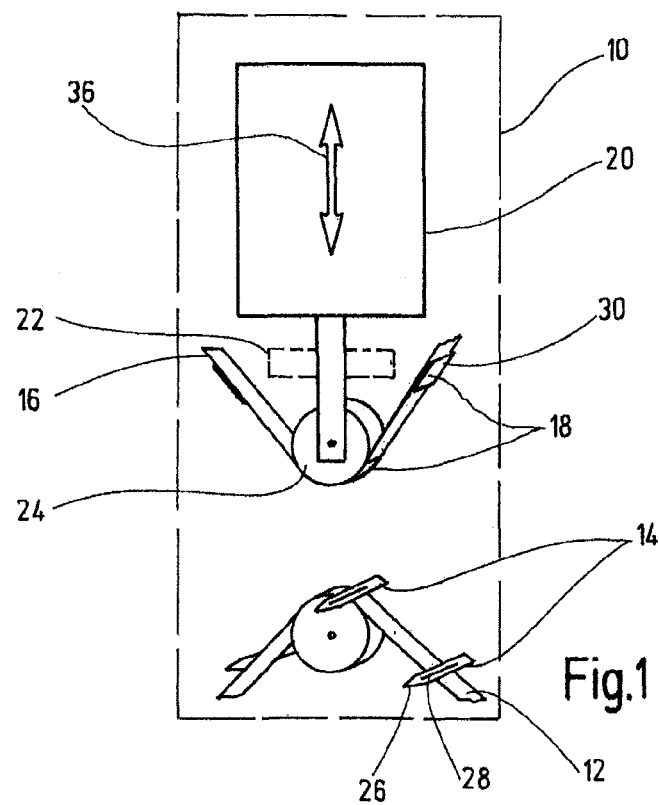
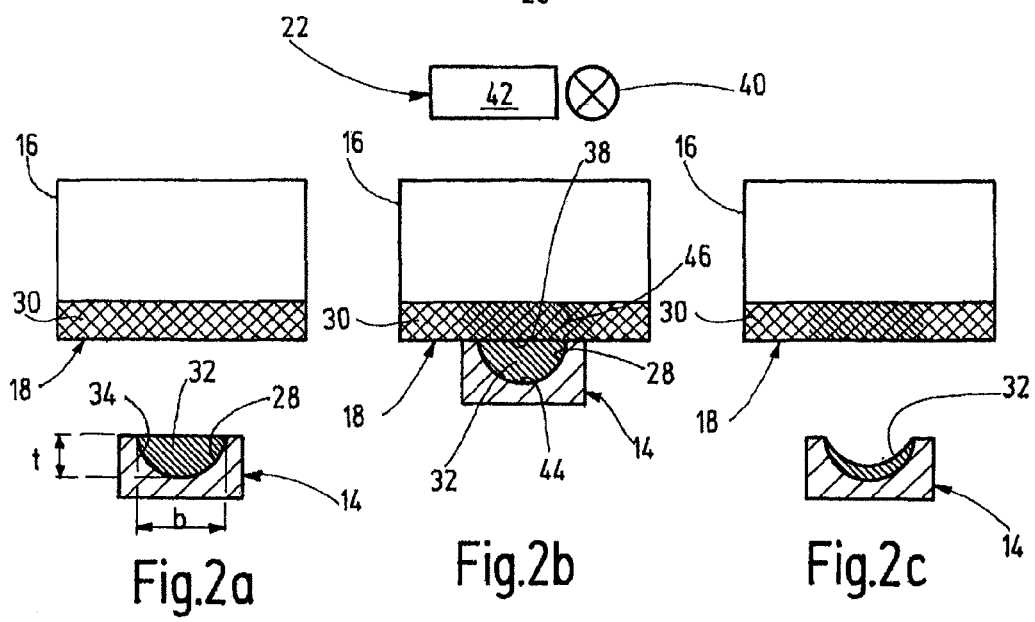

SYSTEM AND METHOD FOR ANALYZING A BODY FLUID

CROSS-REFERENCE TO RELATED APPLICATIONS

This application is a continuation of International Patent Application No. PCT/EP2010/050395, filed Jan. 14, 2010, which claims the benefit and priority of European Patent Application No. 09150807.7, filed Jan. 16, 2009. The entire disclosures of the above applications are incorporated herein by reference.

BACKGROUND

The invention concerns a system or a device for analyzing a body fluid comprising a collecting element which receives the fluid in a reservoir, a test element designed to detect an analyte in the fluid, a transfer device for making a fluidic connection between the collecting element and the test element, and a detection unit which detects an analyte-specific measurement signal on the test element during a measurement interval. The invention additionally concerns a corresponding analytical method.

Systems for blood sugar tests are described in International Application Publication No. WO 2005/084530, Calasso et al, published Sep. 15, 2005 (see also U.S. Patent Application Publication No. 2007/0038149, Calasso et al., published Feb. 15, 2007), in which an integrated combination of a collecting element with an analytical test zone is described in which after the collecting process, sample transfer is intended to take place by deformation of a fluid-conducting channel. However, it makes no reference to the boundary conditions for sample transfer in particular for components that are physically separated from one another before and/or after the measurement. Furthermore, problems may arise with regard to providing and disposing of the consumables due to the integrated arrangement.

SUMMARY

Starting from this the object of the invention is to further develop the products and methods known in the prior art and specify a configuration which is also optimized with regard to provision/disposal of the consumables as well as with regard to reproducible measurement results. Combinations of features described herein are proposed to achieve this object.

The invention is based on the realization that the success of a measurement depends decisively on the fact that the test element essentially always remains loaded with sample fluid over the measurement period. Accordingly it is proposed that the transfer device permanently brings the test element into contact with the body fluid located in the reservoir during the measurement interval so that a liquid column is maintained on a detection area of the test element, and that the transfer device is configured to physically separate the test element and the collecting element from one another after the measurement interval. An adequate liquid volume on the detection area allows reaction processes and in particular diffusion processes to proceed uniformly without layer thickness effects still playing any significant role also with regard to tolerances. The liquid column stands on or over the surface of the test element and thus has a liquid level in a space delimited by the collecting element. The use of separate elements for liquid collection and analytical detection also dictates that they are actively brought together thus also allowing the start of the reaction to be exactly defined. At the same time a simplified handling is also ensured in advance also with regard to sterilization and storage while the separation after the measurement allows disposal to take place in a form which corresponds to the previous provision so that storage is also facilitated. Last but not least contamination of the collecting element with the test chemistry and thus a hazard upon body contact or a reduction of hydrophilic properties is avoided in this configuration.

Advantageously the liquid volume of the reservoir is defined such that the liquid column over the detection area does not fall below a minimum height for the duration of the measurement interval. In this connection it is advantageous when the minimum height of the liquid column is more than 10 µm, preferably more than 50 µm. This also allows a compensation for production-related tolerances and the minimum height below which diffusion processes still play an important role is reliably exceeded.

The test element is basically larger than the actually detected detection area. In order to avoid a site dependency, the test field should be designed such that the body fluid is distributed two-dimensionally over a spreading area during the measurement interval while ensuring that the size of the spreading area and the volume of the reservoir are matched so that a liquid column is maintained over the detection area.

Also in this connection it is advantageous when the reservoir has a depth between 50 and 150 µm, a width between 50 and 150 µm and a length of more than 1 mm, preferably about 2 mm. For a reliable detection while at the same time limiting the required amount of sample it is also advantageous when the detection area has a size in the range of 0.1 mm$^2$ to 1 mm$^2$.

It is advantageous from the perspective of measurement technology when the analyte-specific measurement signal is detected within a period of 0 to 15 s after making the fluidic connection between the collecting element and test element. In this connection it is possible to determine the measurement interval as being when the change in the measurement signal per unit of time has reached a predefined value.

A particularly preferred embodiment provides that the collecting element and test element are spaced apart as separate components in an initial state i.e. are physically separated from one another and that the fluidic connection can be made by reducing the spacing while actively moving the collecting element and/or the test element. This initial separation of the components also gives rise to many advantages with regard to simplified manufacturing methods and applications.

In order to take samples independently of the test chemistry, it is advantageous when the fluid is taken up by a lancing process and when the fluidic connection of the collecting element to the test element is not made until after the lancing process.

The reservoir is advantageously formed by a capillary structure, in particular a linear capillary channel or capillary gap. Furthermore, it is advantageous when the detection area is configured as a dry chemistry layer in particular based on enzymes for a photometric detection and when the collecting element is provided with a hydrophilic coating at least in the area of the reservoir.

Advantages for use also result from the fact that the collecting element and the test element can be separated again from one another after the measurement interval for example for a separate disposal as single use parts. This preferably takes place by means of the transfer device which brings the initially separated components into a defined contact state for the measurement, which, however, is no longer required after completion of the measurement.

With regard to the process the object stated above is achieved by the following steps:
- a fluidic connection is made between a collecting element containing the body fluid in a reservoir and a test element designed to detect an analyte in the body fluid,
- an analyte-specific measurement signal is detected on the test element during a measurement interval,
- the test element is permanently brought into contact with the body fluid located in the reservoir during the measurement interval so that a column of liquid is maintained on the detection area of the test element,
- the test element and the collecting element are separated from one another after the measurement interval.

DRAWINGS

The invention is elucidated in more detail in the following on the basis of an embodiment example shown schematically in the drawing.

FIG. 1 shows a diagnostic analytical system in a simplified diagrammatic representation;

FIG. 2 shows different relative positions of a collecting element and of a test element of the analytical system during the measurement process in cross-section;

DETAILED DESCRIPTION

Figure 3:
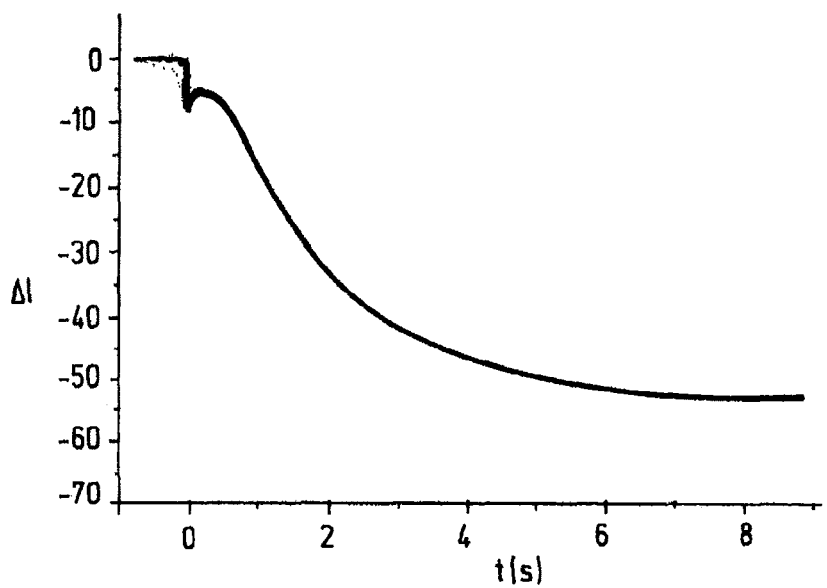
FIG. 3 shows a measurement signal as a function of time.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

The analytical system 10 shown in FIG. 1 comprises in the form of a hand-held device for carrying out blood sugar tests, a carrier tape 12 with a plurality of collecting elements 14 for body fluid (blood or tissue fluid) as well as a separate carrier tape 16 for storing a corresponding number of test elements 18, a sample transfer device 20 and a detection unit 22. A collecting element 14 and a test element 18 can be provided each time for single use at a tape deflector 24 by tape transport. The sample transfer device 20 is in this case configured such that the active test element 18 always remains loaded with body fluid during a measurement interval.

The carrier tapes 12, 16 with the collecting elements 14 and test elements 18 respectively located thereon can be provided in the form of respective tape cassettes so that they can be separately stored and disposed of. Other forms of a separate storage for example in a stacked form are also conceivable. The separate arrangement enables the collecting elements 14 to be sterilized independently of the test elements 18 for example by means of energy-rich irradiation. Moreover, a separate material-tight packaging can also guarantee longer storage times without disadvantages to quality.

The collecting elements 14 can be designed to receive body fluid directly on site. For this purpose the collecting elements 14 can each have a tip 26 for a skin incision and a reservoir for receiving body fluid in the form of a longitudinally semi-open capillary 28. It is basically also possible to load the collecting elements indirectly with the body fluid as intermediate carriers.

The test elements 18 are provided as test fields with a dry chemistry layer 30 based on enzymes for an optical glucose detection. The detection based on a color change can take place through transparent structures by means of a photometric detection unit 22 as described for example in more detail in European Publication No. EP 1760469 A1, Petrich, published Mar. 7, 2007 (see also U.S. Pat. No. 7,708,948, Petrich, issued May 4, 2010).

FIG. 2 shows three different process stages when using the collecting and test elements arranged in pairs.

In an initial state according to FIG. 2a the collecting element 14 is physically separated at a distance from the test element 18. The capillary 28 is filled with body fluid 32. In order to facilitate the uptake of fluid, it is possible to provide the surface of the collecting element 14 with a hydrophilic coating 34 at least in the area of the capillary 28. Typical dimensions of the capillary 28 for the special purpose are about 120 μm in width b, about 80 μm in depth t and about 2 mm in length.

In a next step according to FIG. 2b the measurements are registered. For this purpose a fluidic connection is made between the collecting element 14 and the test element 18 for a sample transfer by means of an actuator of the transfer device 20 symbolized by the double arrow 36 in FIG. 1 while reducing the distance between them. This is carried out such that the open side of the capillary 28 is placed on the dry chemistry layer 30 and the area loaded with body fluid 32 forms a detection area 38 having a surface area of about 0.2 mm$^2$ for recording the photometric measurements. The measurement takes place in the contact state of the collecting element 14 on the rear side through the transparent carrier tape 16. For this purpose the detection unit 22 has a light source 40 and a light receiver 42 in a reflectometric arrangement.

The maintenance of the contact state ensures that a liquid column 44 delimited by the capillary 28 is maintained on the detection area 38 during the measurement interval. The liquid column 44 is thus located in a space delimited by the collecting element 14 above the wetted surface of the test element 18. In this connection the dimensions of the capillary 28 are selected such that the liquid column 44 does not fall below a minimum height of about 50 μm at least over the area of the optically scanned detection area 38. In this connection an adequate capillary volume as a reservoir also takes into consideration the fact that the dry chemistry layer 30 is provided with a spreading surface which distributes the body fluid 32 two-dimensionally in a spreading area 46.

As shown in FIG. 2c, the transfer device 20 is also designed to actively separate the collecting element 14 and the test element 18 again after the measurement by means of the actuator 36. This enables them to be separately disposed of in accordance with the initial situation. In the embodiment example shown this is carried out in the form of separate tapes 12, 16 which considerably simplify re-storage. The user can thus insert consumables into the device 10 which enable a plurality of tests to be carried out without complicated handling.

FIG. 3 shows the time course of a signal recorded by means of the detection unit 22. The measurement interval includes at least one such time window in which it is possible to observe a signal time course based on a reaction of the analyte (glucose). This can be carried out with the aim of analyzing the reaction kinetics or to directly determine a concentration value.

The detection is based on a color change of the detection area 38 due to the analyte-specific reaction which is recorded as a grey value time course ΔI in reflectance. Whereas initially a blank value or zero value is observed in the separated state, an analyte-specific decrease in the signal occurs upon contact according to FIG. 2b which finally approaches a characteristic end value for the glucose concentration. The duration of the measurement interval in which the analyte-specific signal is recorded, can be defined by a predefined threshold value for the signal change per unit of time. For example the measurement could be discontinued when the signal changes by less than 3% per second. The duration of the measurement is then usually less than 8 s.

Figure 4:
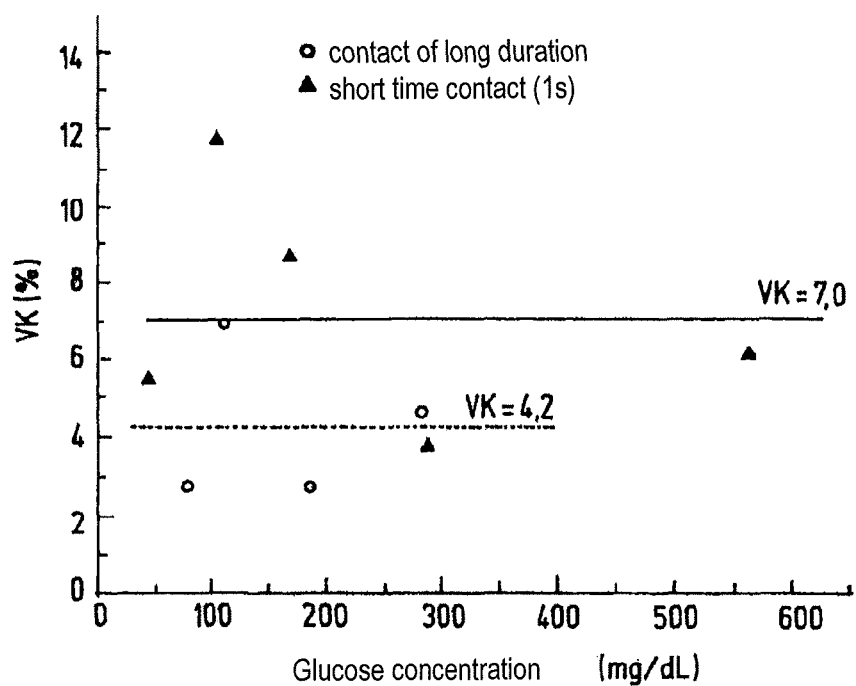
FIG. 4 shows a measurement diagram of a comparative example.

In a comparative experiment measurements were carried out with a contact of long duration according to the invention between the collecting element and test element and measurements were carried out with a short time contact (about 1 s) after filling the capillary with test fluid of various glucose concentrations. FIG. 4 shows the scattering of the experimental results in the form of the coefficients of variation of the glucose concentration. This shows that there is a significantly lower mean variation of 4.2% for the long lasting contact compared to a mean variation of 7% for the short time contact. Hence, the reaction processes proceed more reproducibly due to maintenance of the liquid column 32. A comparatively large minimum height of the liquid layer ensures that diffusion processes proceed substantially independently of the layer height whereas in the case of a short time contact quasi in the form of slapping the fluid on the dry chemistry layer 30 there may be local variations in the processes.

What is claimed is:

1. A system for analyzing a body fluid comprising
   a collecting element which receives the body fluid in a reservoir,
   a test element designed to detect an analyte in the body fluid,
   a transfer device for making a fluidic connection between the collecting element and the test element, and
   a detection unit which detects an analyte-specific measurement signal on the test element during a measurement interval, wherein
   the transfer device permanently brings the test element into contact with the body fluid located in the reservoir during the measurement interval so that a liquid column is maintained on a detection area of the test element,
   the liquid volume of the reservoir is defined such that the liquid column over the detection area does not fall below a minimum height for the duration of the measurement interval; and
   the transfer device is configured to physically separate the test element and the collecting element from one another after the measurement interval.

2. The system according to claim 1, wherein the minimum height of the liquid column is more than 10 μm, preferably more than 50 μm.

3. The system according to claim 1, wherein the test element is designed to distribute the body fluid two-dimensionally over a spreading area during the measurement interval, and that the size of the spreading area and the volume of the reservoir are matched in such a manner that a liquid column is maintained over the detection area during the measurement interval.

4. The system according to claim 1, wherein the reservoir has a depth between 50 and 150 μm, a width between 50 and 150 μm and a length of more than 1 mm.

5. The system according to claim 4, wherein the length is about 2 mm.

6. The system according to claim 1, wherein the detection area has a size in the range of 0.1 $mm^2$ to 1 $mm^2$.

7. The system according to claim 1, wherein the analyte-specific measurement signal is detected within a period of 0 to 15 s after making the fluidic connection between the collecting element and test element.

8. The system according to claim 1, wherein the end of the measurement interval is determined as being when the change in the measurement signal per unit of time has reached a predefined value.

9. The system according to claim 1, wherein the collecting element and test element are spaced apart as separate components in an initial state and that the fluidic connection can be made while actively moving the collecting element and/or the test element.

10. The system according to claim 1, wherein the fluid is taken up by a lancing process and that the fluidic connection of the collecting element to the test element is not made until after the lancing process.

11. The system according to claim 1, wherein the reservoir is formed by a capillary structure, in particular a linear capillary channel or capillary gap which is preferably open on one side.

12. The system according to claim 1, wherein the detection area is formed by a dry chemistry layer in particular based on enzymes for a photometric detection.

13. The system according to claim 1, wherein the collecting element is provided with a hydrophilic coating at least in the area of the reservoir.

14. The system according to claim 1, wherein the collecting element and the test element can be separated again from one another after the measurement interval preferably by means of the transfer device.

* * * * *